United States Patent [19]

Bauer et al.

[11] 3,959,475

[45] May 25, 1976

[54] SUBSTITUTED 1,3-DIHYDROSPIRO(ISOBENZOFURAN)S

[75] Inventors: Victor J. Bauer, Somerville; Raymond W. Kosley, Jr., Convent, both of N.J.

[73] Assignee: American Hoechst Corporation, Bridgewater, N.J.

[22] Filed: Sept. 3, 1974

[21] Appl. No.: 502,650

Related U.S. Application Data

[63] Continuation-in-part of Ser. No. 424,117, Dec. 12, 1973, abandoned.

[52] U.S. Cl. ............................ 424/267; 260/293.58; 260/326.24; 260/326.5 D; 260/346.2 R; 424/274; 424/285
[51] Int. Cl.² ....................................... C07D 491/10
[58] Field of Search ................ 260/293.58, 326.24, 260/326.5 D, 346.2 R; 424/267, 274, 285

[56] References Cited
UNITED STATES PATENTS 3,686,186  8/1972  Houlihan et al. .............. 260/293.58

OTHER PUBLICATIONS

Braenden et al., Bull. World Health Org. 13, 937, 956–961, (1955).

*Primary Examiner*—G. Thomas Todd
*Attorney, Agent, or Firm*—Curtis, Morris & Safford

[57] ABSTRACT

Novel substituted 1,3-dihydrospiro[isobenzofuran]s and methods of preparing the same are described. These compounds are useful as antidepressants, tranquilizers, analgetic agents and intermediates therefor.

48 Claims, 1 Drawing Figure

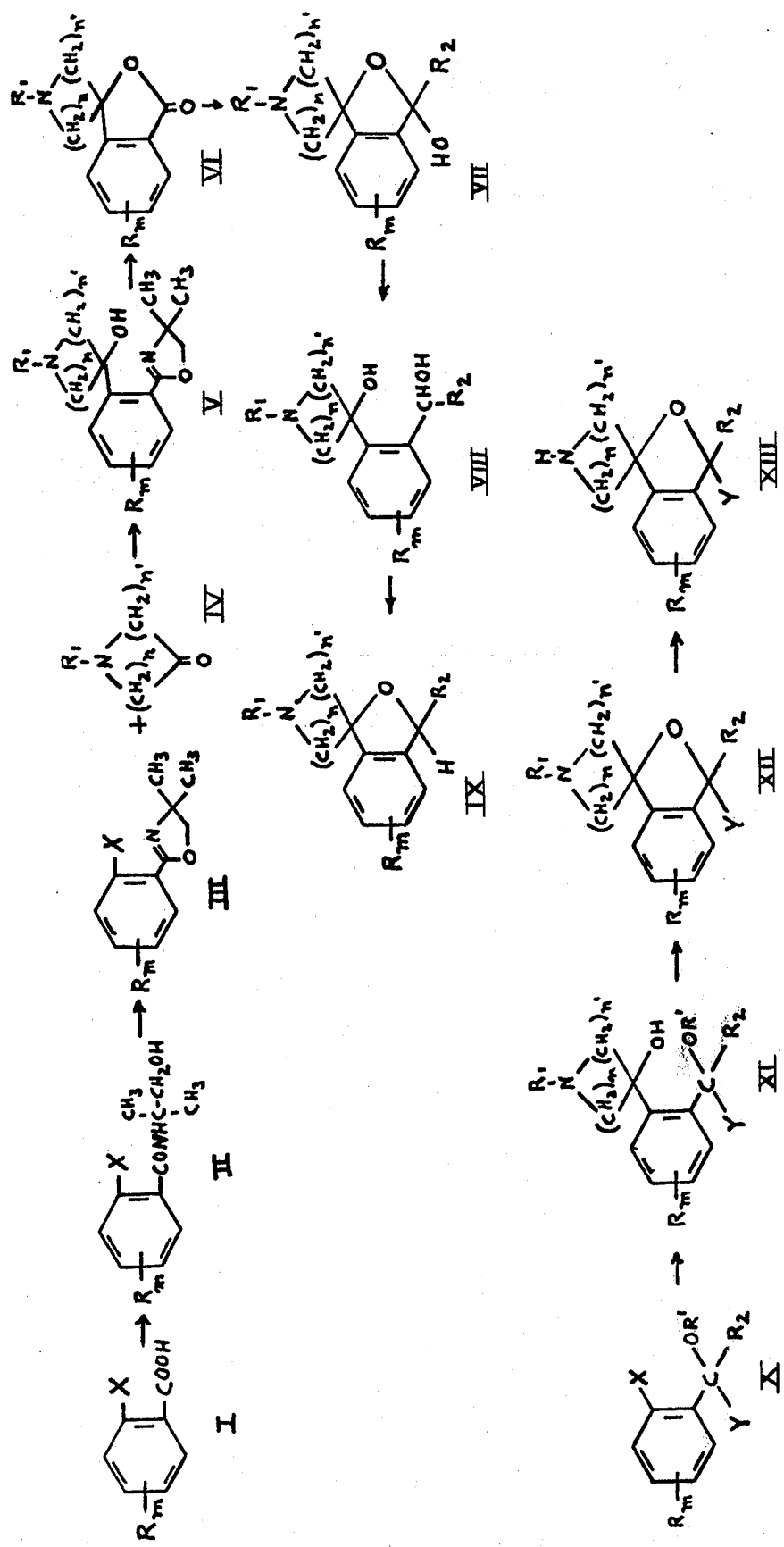

SUBSTITUTED 1,3-DIHYDROSPIRO(ISOBENZOFURAN)S

This is a continuation in part of application Ser. No. 424,117 filed Dec. 12, 1973 now abandoned.

This invention relates to novel substituted 1,3-dihydrospiro[isobenzofuran]s which are useful as antidepressants, tranquilizers, analgetic agents and as intermediates therefor, to methods of preparing the same, to methods of treatment with pharmaceutically effective amounts thereof, and to pharmaceutical compositions containing such compounds as essential active ingredients.

To the best of our knowledge, the compounds of this invention have not heretofore been described or suggested. Spiro[phthalan-piperidine]s of the formula

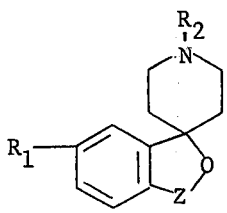

in which $R_1$ is hydrogen, lower alkyl, lower alkoxy, halogen or trifluoromethyl, $R_2$ is hydrogen or benzyl, and Z is —$CH_2$— or —CO—, described by W. J. Houlihan et al. in U.S. Pat. No. 3,686,186 are outside the scope of the invention. The same applies to the natural product of the formula

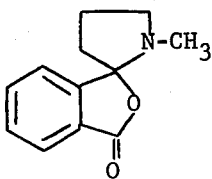

described by Y. Inubushi et al. [Chem. and Pharm. Bull. (Japan), 12, 749 (1964)].

This invention relates to novel substituted 1,3-dihydrospiro[isobenzofuran]s of the formula:

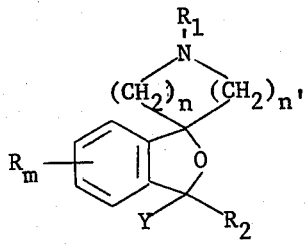

in which

R is hydrogen, alkyl of 1 to 6 carbon atoms, alkoxy of 1 to 6 carbon atoms, trifluoromethyl, halogen, hydroxy, or methylenedioxy;

$R_1$ is hydrogen, alkyl of 1 to 6 carbon atoms, cycloalkylalkyl of 4 to 8 carbon atoms, alkenyl of 3 to 6 carbon atoms, phenylalkyl of the formula $(CH_2)_x$—PhR, diphenylalkyl of the formula $(CH_2)_m$—CH(PhR)$_2$, diphenylmethoxyalkyl of the formula —$(CH_2)_m$—OCHPh$_2$, alkanoyl of 2 to 6 carbon atoms, phenylalkanoyl of the formula —CO(CH$_2$)$_x$—PhR, benzoyl of the formula —COPhR, benzoylalkyl of the formula —(CH$_2$)$_m$—COPhR, phenylhydroxyalkyl of the formula —(CH$_2$)$_m$CHOHPhR, alkoxycarbonyl of 2 to 6 carbon atoms, phenyloxycarbonyl or cycloalkylcarbonyl of 4 to 8 carbon atoms;

$R_2$ is alkyl of 1 to 6 carbon atoms or phenyl of the formula —PhR;

Y is hydrogen, alkyl of 1 to 6 carbon atoms, alkoxy of 1 to 6 carbon atoms, hydroxy or phenyl of the formula PhR;

Ph is phenyl;

m, n and n' are integers from 1 to 3; and x is an integer from 1 to 4, as well as the optical antipodes and the pharmaceutically acceptable acid addition salts thereof.

The compounds that are preferred are those in which R is hydrogen, alkyl of 1 to 3 carbon atoms, alkoxy of 1 to 3 carbon atoms, fluorine, chlorine, trifluoromethyl, hydroxy or methylendioxy; $R_1$ is hydrogen, alkyl of 1 to 6 carbon atoms, cycloalkylalkyl of 4 to 5 carbon atoms, alkenyl of 3 to 5 carbon atoms, phenylalkyl of the formula —(CH$_2$)$_m$—PhR, diphenylalkyl of the formula —(CH$_2$)$_m$—CH—(PhR)$_2$, alkanoyl of 2 to 4 carbon atoms, phenylalkanoyl of the formula —CO(CH$_2$)$_m$—PhR, benzoylalkyl of the formula —(CH$_2$)$_m$—COPhR, benzoyl of the formula —COPhR, alkoxycarbonyl of 2 or 3 carbon atoms or cycloalkylcarbonyl of 4 to 7 carbon atoms; $R_2$ is alkyl of 1 to 3 carbon atoms or phenyl of the formula PhR'', R'' being hydrogen, alkyl of 1 to 3 carbon atoms, alkoxy of 1 to 3 carbon atoms, halogen, methylenedioxy or trifluoromethyl; Y is hydrogen, alkyl of 1 to 3 carbon atoms, alkoxy of 1 to 4 carbon atoms or phenyl of the formula PhR''.

Acids useful for preparing the pharmaceutically acceptable acid addition salts of the invention include inorganic acids such as hydrochloric, hydrobromic, sulfuric, nitric, phosphoric, and perchloric acids, as well as organic acids such as tartaric, citric, acetic, succinic, maleic, fumaric and oxalic acids.

Some compounds within the scope of this invention have greater pharmaceutical activity than others. The latter, such as those in which Y is hydroxy or $R_1$ is alkanoyl, phenylalkanoyl, benzoyl, alkoxycarbonyl, benzyloxycarbonyl, phenoxycarbonyl, benzyl or substituted benzyl, are nevertheless desirable as intermediates for the preparation of the more active compounds, as will become apparent from the following description of several methods of preparation, which is made with reference to the attached drawing in which, with the exceptions noted, R, $R_1$, $R_2$, Y, m, n and n' are as defined previously and X is halogen, preferably chlorine or bromine.

METHOD A

An o-halobenzoic acid I, in which R is hydrogen, alkyl, alkoxy, halogen, trifluoromethyl or methylenedioxy and m is 1 or 2, is converted to the corresponding benzoyl chloride by treatment with a halogenating agent such as thionyl chloride, phosphorus pentachloride, or oxalyl chloride at a temperature of 0° to 120° for a time of 0.25 to 24 hours in the presence or absence of a catalyst such as dimethylformamide with or without a solvent inert to the reactants such as ether, toluene, or dichloromethane. The benzoyl chloride is then allowed to react with 2-amino-2-methyl-1- propanol at a temperature of from −20° to 35° with or without an acid-neutralizing agent such as sodium bicarbonate in the presence of a solvent such as dichloromethane or benzene to provide an o-halo-N-(1-hydroxy-2-methyl-2-propyl)benzamide II. It will be readily appreciated by those skilled in the art that the time and temperature necessary to complete the reaction in this and subsequent steps are interrelated and dependent upon the structures and compositions of the reaction components and the solvent.

The o-halo-N-(1-hydroxy-2-methyl-2-propyl)benzamide II is cyclized to an o-halophenyloxazoline III by treatment with a dehydrating agent such as thionyl chloride, phosgene, or phosphorus oxychloride at a temperature of −20° to 40° in the presence or absence of a solvent such as toluene, pyridine, or chloroform for a time of 0.5 to 24 hours.

The o-halophenyloxazoline III is converted to the Grignard reagent under the usual conditions, i.e. by reaction with magnesium at a temperature of preferably 25° to 100° in a solvent such as ether or tetrahydrofuran for a time of preferably 0.25 to 24 hours with or without the assistance of an initiator such as iodine or 1,2-dibromoethane. Reaction of the Grignard reagent with a cycloazalkanone IV at a temperature of −60° to 100° for a time of 0.25 hours to 24 hours, provides an oxazolinylphenylcycloazalkanol V.

The oxazolinylphenylcycloazalkanol V is treated with an acid such as aqueous hydrochloric or sulfuric acid at a temperature of 25° to 125° for a time of 10 minutes to 24 hours with or without a solvent such as water, ethanol, or acetic acid to provide a 1,3-dihydrospiro]isobenzofuran-cycloazalkane]-3-one VI.

The 1,3-dihydrospiro]isobenzofuran-cycloazalkane]-3-one VI is allowed to react with an organometallic reagent such as alkyl- or arylmagnesium halide or an alkyl- or aryllithium under the normal conditions, e.g., at a temperature of −60° to 100° with a solvent such as hexane, toluene, ether, or tetrahydrofuran for a time of 10 minutes to 24 hours, to provide a 1,3-dihydro-3-hydroxyspiro[isobenzofuran-cycloazalkane] VII.

The 1,3-dihydro-3-hydroxyspiro[isobenzofuran-cycloazalkane] VII is converted by a reducing agent such as lithium aluminum hydride or sodium bis(2-methoxyethoxy)aluminum hydride at a temperature of 0° to 110° in a solvent such as toluene, ether or tetrahydrofuran for a time of 10 minutes to 24 hours to an o-hydroxyalkylphenylcycloazalkanol VIII.

The o-hydroxyalkylphenylcycloazalkanol VIII is treated with an acid, such as hydrochloric, formic, or p-toluenesulfonic acid with or without a solvent, such as toluene or acetic acid at a temperature of 25° to 150°, preferably 25°–110° for a time of 5 minutes to 24 hours, preferably 5 minutes to 3 hours, to provide a 1,3-dihydrospiro[isobenzofuran-cycloazalkane] IX.

METHOD B

An o-halobenzylalcohol X in which R and *m* are defined as in the description of Method A, Y is hydrogen or alkyl, and R' is hydrogen, alkyl or tetrahydropyranyl, is converted to the dilithium derivative by treatment with an alkyllithium of preferably 1 to 6 carbon atoms at a temperature of −30° to 100° for a time of 10 minutes to 12 hours in a solvent such as ether, hexane, or tetrahydrofuran. Alternatively, an o-halobenzyl ether X is converted to the lithium derivative or Grignard reagent in the usual manner. The resulting lithium o-lithiobenzalkoxide, o-lithiobenzyl ether, or Grignard reagent is allowed to react with a cycloazalkanone IV for a time of 0.25 to 24 hours under reaction conditions which are commonly used for this type of reaction, e.g., at a temperature of −80° to 100°, preferably −80° to 20°, in a solvent such as ether, tetrahydrofuran, or hexane to provide an o-hydroxyalkylphenylcycloazalkanol or its ether XI.

The o-hydroxyalkylphenylcycloazalkanol or its ether XI is then cyclized to a 1,3-dihydrospiro[isobenzofuran-cycloazalkane] XII by acid treatment as in Method A, above.

METHOD C

An N-benzyl-1,3-dihydrospiro[isobenzofuran-cycloazalkane] XII in which $R_1$ is $CH_2PhR$, is hydrogenated at a pressure of 1 to 15 atmospheres with a catalyst such as palladium on carbon in a solvent such as ethanol, acetic acid, or water in the presence of an acid such as hydrochloric or perchloric acid at a temperature of 25° to 100° until hydrogen uptake ceases to form the corresponding 1,3-dihydrospiro[isobenzofuran-cycloazalkane] XIII.

METHOD D

A 1,3-dihydrospiro[isobenzofuran-cycloazalkane] XIII can be prepared by treating an N-substituted 1,3-dihydrospiro[isobenzofuran-cycloazalkane] XII with a chloroformate, e.g., an alkyl- or phenylchloroformate, at a temperature of 25° to 125°C. for 0.25 to 24 hours in a solvent such as toluene or benzene to provide the corresponding N-alkoxycarbonyl- or N-phenyloxycarbonyl-1,3-dihydrospiro[isobenzofuran-cycloazalkane], which is then treated with a base such as sodium or potassium hydroxide in a solvent such as water or ethanol, or with an acid such as hydrogen bromide in acetic acid, for 0.25 to 24 hours at a temperature of 25° to 125°C.

METHOD E

An N-unsubstituted 1,3-dihydrospiro[isobenzofuran-cycloazalkane] XIII prepared by Method C and D can be reacted in known manner with an alkanoyl chloride or anhydride, aroyl chloride or anhydride, aralkanoyl chloride, alkyl halide, alkenyl halide, cycloalkanoyl halide, aralkyl halide or aroylalkyl halide, to provide the corresponding N-alkanoyl, N-aroyl, N-aralkanoyl, N-alkyl, N-alkenyl, N-cycloalkanoyl, N-aralkyl or N-aroylalkyl derivative.

METHOD F

The N-alkoxycarbonyl-, N-aryloxycarbonyl-, N-alkanoyl-, N-cycloalkylcarbonyl-, N-aroyl-, N-aralkanoyl-1,3-dihydrospiro[isobenzofuran-cycloazalkanes] prepared by Methods D and E can be reduced in a known manner with a reagent such as lithium aluminum hydride to the corresponding N-alkyl-, N-cycloalkylalkyl-, or N-aralkanyl-1,3-dihydrospiro[isobenzofuran-cycloazalkanes].

METHOD G

An N-substituted-1,3-dihydro-3-hydroxyspiro[isobenzofuran-cycloazalkane] VII is heated with an aliphatic mono-alcohol under acid catalysis, for example in the presence hydrochloric acid under the normal conditions of this type of reaction, to provide the corresponding ether XII.

METHOD H

An N-substituted 1,3-dihydrospiro[isobenzofuran-cycloazalkane] XII in which R is alkoxy is heated with an acid, for example hydrobromic acid or aluminum tribromide, under the normal conditions of hydrolyzing reactions to provide the corresponding hydroxy compound.

METHOD I

A 1,3-dihydrospiro[isobenzofuran-cycloazalkane] XII where R is methoxy can be cleaved to the corresponding compound XII where R is hydroxy by heating with sodium thioethoxide in the presence of a solvent.

METHOD J

An N-substituted 1,3-dihydrospiro[isobenzofuran-cycloazalkane] XII in which Y is hydrogen is treated with an alkyllithium of from 1 to 6 carbon atoms, in a solvent such as tetrahydrofuran, at a temperature of from −50° to 50°C., for from a few minutes to several hours, to produce the corresponding lithium derivative. The lithium derivative is alkylated in situ, at a temperature of from −25° to 50°C., for from several minutes to 24 hours to give the corresponding compound in which Y is alkyl.

Compounds of the present invention are useful in the treatment of depression in mammals, as demonstrated by their ability to inhibit tetrabenzazine-induced depression in mice [International Journal of Neuropharmacology, 8, 73 (1969)], a standard assay for useful antidepressant properties. Thus, for instance, the minimum effective dosages (MED) at which the following compounds inhibit ptosis of tetrabenzazine-induced depression in mice are:

|  | MED, mg/kg |
|---|---|
| 1,3-dihydro-3-phenylspiro[isobenzofuran-1,4′-piperidine] | 0.5 |
| 1,3-dihydro-1′-methyl-3-phenylspiro[isobenzofuran-1,4′-piperidine] | 1.0 |
| 1,3-dihydro-1′-ethyl-3-phenylspiro[isobenzofuran-1,4′-piperidine] | 5.0 |
| 1,3-dihydro-1′-methyl-3-(4-methoxyphenyl)spiro[isobenzofuran-1,4′-piperidine] | 2.5 |
| 1,3-dihydro-1′-methyl-3-phenylspiro[isobenzofuran-1,3′pyrrolidine] | 1.6 |
| 1,3-dihydro-1′-butyl-3-phenylspiro[isobenzofuran-1,4′-piperidine] | 10.0 |
| 1,3-dihydro-3-p-fluorophenylspiro[isobenzofuran-1,4′-piperidine] | 0.5 |
| 1,3-dihydro-1′-cyclopropylmethyl-3-phenylspiro[isobenzofuran-1,4′-piperidine] | 2.5 |
| 1,3-dihydro-3-phenylspiro[isobenzofuran-1,3′-pyrrolidine] | 0.3 |
| 1′-cyclopropylmethyl-1,3-dihydro-3-phenylspiro[isobenzofuran-1,3′-pyrrolidine] hydrobromide | 0.7 |
| 1,3-dihydro-3-p-tolylspiro[isobenzofuran-1,4′-piperidine] | 0.8 |
| 1,3-dihydro-6-fluoro-3-p-fluorophenylspiro[isobenzofuran-1,4′-piperidine] | 0.8 |
| 1,3-dihydro-6-methoxy-3-phenylspiro[isobenzofuran-1,4′-piperidine] | 0.3 |
| 1,3-dihydro-3-p-fluorophenyl-1′-methylspiro[isobenzofuran-1,4′-piperidine] | 1.4 |
| 1,3-dihydro-3-p-methoxyphenylspiro[isobenzofuran-1,4′-piperidine] | 2.0 |
| 1,3-dihydro-1′,3-dimethyl-3-phenylspiro[isobenzofuran-1,4′-piperidine] hydrobromide | 9.5 |

Compounds of the present invention are further useful as tranquilizers due to their depressant action on the central nervous system of mammals. This activity is demonstrated in the mouse observation procedure, a standard assay for CNS depressants [Psychopharmacologia, 9, 259 (1966)]. Thus, for instance, the minimum effective dose (MED) at which 1,3-dihydro-1′-(2-phenylethyl)-3-phenylspiro-[isobenzofuran-1,4′-piperidine] displays significant effects on behavior and reflex depression together with muscle relaxation is 20 mg/kg. Similarly, MED's of other compounds are:

|  | MED, mg/kg |
|---|---|
| 1,3-dihydro-1′-[3-(4-fluorobenzoyl)propyl]-3-phenylspiro[isobenzofuran-1,4′-piperidine] | 10.0 |
| 1,3-dihydro-1′,3-dimethylspiro[isobenzofuran-1,4′-piperidine] | 25.0 |
| 1,3-dihydro-1′-benzyl-3,5-dimethoxy-3-phenylspiro-[isobenzofuran-1,4′-piperidine] | 20.0 |
| 1,3-dihydro-1′-cyclopropylmethyl-3-phenylspiro-[isobenzofuran-1,4′-piperidine] | 2.5 |
| 1,3-dihydro-1′-propyl-3-phenylspiro[isobenzofuran-1,4′-piperidine] | 25.0 |
| 1,3-dihydro-1′-benzyl-3-(4-fluorophenyl)spiro-[isobenzofuran-1,4′-piperidine] | 25.0 |

The utility of compounds of the present invention as tranquilizers is also demonstrated by their ability to inhibit foot shock-induced rage [Arch. Int. Pharmacodynam. et de Therap., 142, 30 (1963)] and to antagonize the toxicity of amphetamine in aggregated situations in mice [J. Pharmacol. Exp. Therap., 87, 214 (1946)]. Thus, at doses of 3 and 10 mg/kg., respectively of 1,3-dihydro-1′-methyl-3-phenylspiro[isobenzofuran-1,4′piperidine] and 1,3-dihydro-3-phenylspiro[isobenzofuran-1,4′-piperidine], 50% of mice are protected from foot-shock-induced rages. Doses of 27,0.9, and 1.0 mg/kg. of 1,3-dihydro-1′-methyl-3-phenylspiro[isobenzofuran-1,4′-piperidine], 1,3-dihydro-1′-[3-(4-fluorobenzoyl)propyl]-3-phenylspiro[isobenzofuran-1,4′-piperidine], and 1,3-dihydro-1′-(2-phenethyl)-3-phenylspiro[isobenzofuran-1,4′-piperidine], respectively, antagonize amphetamine toxicity in 50% of mice. These data illustrate that 1,3-dihydrospiro[isobenzofuran]s of this invention are useful as tranquilizers in mammals when administered in amounts ranging from 0.1 to 50 mg/kg. of body weight per day.

Compounds of the present invention are also useful as analgesic agents due to their ability to alleviate pain in mammals. The analgesic utility of compounds of this invention is demonstrated in the phenyl-o-quinone-induced writhing assay in mice, a standard assay for analgesia [Proc. Soc. Exptl. Biol. Med., 95, 729 (1957)]. Thus, for instance, an approximately 50% inhibition of writhing is effected by an 8.4 mg/kg. dose of 1,3-dihydro-1′-methyl-3-phenylspiro[isobenzofuran-1,4′-piperidine]. Similarly effective are 14.5 mg/kg. and 10.5 mg/kg. doses of 1,3-dihydro-3-phenylspiro[isobenzofuran-1,4′-piperidine] and 1,3-dihydro-1′-(4-fluorobenzoyl)propyl]-3-phenylspiro[isobenzofuran-1,4′-piperidine]. Doses of 50 mg/kg. of 1,3-dihydro-1′-ethyl-3-phenylspiro[isobenzofuran-1,4′-piperidine], 1,3-dihydro-1′,3-dimethyl-3-hydroxyspiro[isobenzofuran-1,4′-piperidine], 1,3-dihydro-3-hydroxy-1′-(2-phenylethyl)-3-phenylspiro[isobenzofuran-1,4′-piperidine], 1,3-dihydro-1′,3-dimethylspiro[isobenzofuran-1,4′-piperidine], 1,3-dihydro-3-(4-methoxyphenyl)- 1′-methylspiro[isobenzofuran-1,4′-piperidine], and 1,3-dihydro-1′-ethoxycarbonyl-3-phenylspiro[isobenzofuran-1,4′-piperidine] exhibit a 79%, 51%, 56%, 57%, 47%, and 52%, respectively, inhibition of writhing. For comparison, aspirin and propoxyphene hydrochloride, known analgesic agents, effect a 34% and 50% inhibition with doses of 60 mg/kg. and 28 mg/kg., respectively. These data illustrate that the 1,3-dihydrospiro[isobenzofuran]s of this invention are useful for the alleviation of pain in mammals when administered in amounts ranging from 1 to about 50 mg per kg. of body weight per day.

The compounds of the present invention may be administered to a patient by any convenient route such as orally, intramuscularly, intravenously, subcutaneously, or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% of the weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or both. A syrup may contain, in addition to the active compounds, sucrose as a sweetening agent, and certain preservatives, dyes and colorings, and flavors. Materials used in preparing these various compositions must be pharmaceutically pure and non-toxic in the amounts utilized.

The invention is further illustrated by the following examples. Temperatures are given in degrees C.

EXAMPLE 1

1,3-Dihydro-3-hydroxy-1'-methyl-3-phenyl-spiro[isobenzofuran-1,4'-piperidine]

a. A mixture of 400 g. of o-bromobenzoic acid, 230 g. of thionyl chloride, and 1 ml. of dimethylformamide is heated slowly to reflux, and then for one hour under reflux. The excess thionyl chloride is distilled under reduced pressure, and the residue is dissolved in 1 l. of dichloromethane. The resulting solution is added dropwise with stirring to a solution of 520 g. of 2-amino-2-methylpropanol in 1 l. of dichloromethane cooled to 0°, and the mixture is stirred for 2 hours at 0° and filtered. The solid is air dried, stirred for 1 hour in 2 l. of warm water, filtered, washed liberally with water, and air dried to an off-white solid, 2-bromo-N-(1-hydroxy-2-methyl-2-propyl)benzamide, m.p. 142°–145°.

b. 254 g. of 2-bromo-N-(1-hydroxy-2-methyl-2-propyl)benzamide are added to 200 ml. of cold (0°) stirred thionyl chloride in the course of 15 minutes. The solution is stirred at 0° for ½ hour and at room temperature for 12 hours, and is then poured into 1.5 l. of ether. The solid which separates is collected, washed with ether, dried, and then added at 0° to 1 l. of 20% aqueous sodium hydroxide. The mixture is extracted with ether, and the ether solution is dried over potassium carbonate and concentrated to an oil. Crystallization from hexane provides colorless crystals, m.p. 39°–40°, of 2-(2-bromophenyl)-4,4-dimethyl-2-oxazoline.

c. A Grignard reagent is prepared by the dropwise addition of a solution of 53.3 g. of 2-(2-bromophenyl)-4,4-dimethyl-2-oxazoline and 500 ml. of anhydrous tetrahydrofuran to a refluxing stirred mixture of 6.2 g. of magnesium shavings and 100 ml. of tetrahydrofuran. Initiation with iodine crystals is sometimes required. After addition, the mixture is heated under reflux for 2 hours. Then, a solution of 25 ml. of 1-methyl-4-piperidone in 25 ml. of tetrahydrofuran is added dropwise, and the solution is heated under reflux for 2 hours and allowed to cool to room temperature. Approximately 25 ml. of saturated aqueous ammonium chloride is added, the mixture is filtered, and the solid is washed with benzene. The combined organic solution is washed with water and saturated aqueous sodium chloride, dried over potassium carbonate, and concentrated to an oil. Crystallization from ethanol gives colorless crystals, m.p. 162°–163°, of 4-[2-(4,4-dimethyl-2-oxazolin-2-yl)-phenyl]-4-hydroxy-1-methylpiperidine.

d. A solution of 6.0 g. of 4-[2-(4,4-dimethyl-2-oxazolin-2-yl)phenyl]-4-hydroxy-1-methylpiperidine and 70 ml. of 3N hydrochloric acid is heated under reflux for 3 hours, cooled to 0°, and made basic with sodium hydroxide. The mixture is extracted with chloroform, and the chloroform solution is dried over potassium carbonate and concentrated to a solid. Recrystallization from benzene provides colorless crystals, m.p. 147°–148°, of 1,3-dihydro-1'-methylspiro[isobenzofuran-1,4'-piperidine]-3-one.

e. A solution of 2.20 g. of 1,3-dihydro-1'-methyl-spiro[isobenzofuran-1,4'-piperidine]-3-one in 60 ml. of dry tetrahydrofuran is added dropwise in the course of 15 minutes to 12 ml. of cold stirred 2M phenyllithium in benzene-ether. The solution is stirred at 0° for 1 hour and at room temperature for 1 hour, diluted with water, and extracted with benzene. The benzene solution is dried over anhydrous potassium carbonate and concentrated to an oil. Trituration with ether followed by recrystallization from ethanol gives colorless crystals, m.p. 182°–183°.

Analysis: Calc. for $C_{19}H_{21}NO_2$ : C 77.62%; H 7.17%; N 4.74%; Found : C 77.45%; H 7.34%; N 4.84%.

EXAMPLE 2

1,3-Dihydro-1'-methyl-3-phenylspiro[isobenzofuran-1,4'-piperidine]

A solution of 8.5 g. of 1,3-dihydro-3-hydroxy-1'-methyl-3-phenylspiro[isobenzofuran-1,4'-piperidine], Example 1, in 150 ml. of tetrahydrofuran is added dropwise in 30 minutes to a stirred suspension of 2.0 g. of lithium aluminum hydride in 150 ml. of anhydrous tetrahydrofuran. The mixture is stirred at room temperature for 30 minutes and at 50° for 1 hour, cooled, diluted cautiously with water, and extracted with chloroform. The chloroform solution is dried over potassium carbonate and concentrated to a solid. Recrystallization from benzene gives colorless crystals, m.p. 190°–191° of 4-hydroxy-4-(α-hydroxy-α-phenyl-2-tolyl)-1-methylpiperidine.

A solution of 4.4 g. of 4-hydroxy-(α-hydroxy-α-phenyl-2-tolyl)-1-methylpiperidine, 30 ml. of glacial acetic acid, and 7.5 ml. of conc. hydrochloric acid is heated under reflux for 10 minutes, cooled to 0°, diluted with water, made basic with sodium hydroxide, and extracted with chloroform. The chloroform solution is dried over potassium carbonate and concentrated to a solid. Recrystallization from hexane gives colorless crystals, m.p. 123°–124°, of 1,3-dihydro-1'-methyl-3-phenylspiro[isobenzofuran-1,4'-piperidine], (hydrochloride salt, m.p. 255°).

Analysis: Calc. for $C_{19}H_{21}NO$: C 81.68%; H 7.58%; N 5.01%; Found : C 81.73%; H 7.65%; N 5.02%.

EXAMPLES 3–22

In the following odd and even numbered examples, the procedures are the same as in Examples 1 and 2, respectively. The compositions and structures of the starting materials I and IV, of the intermediates II, III, V, VI and VIII, and of the final products VII (odd numbered examples) and IX (even numbered examples) are indicated in Table I and shown in Formulae I–IX of the attached drawing.

EXAMPLE 23

1,3-Dihydro-1'-methyl-3-phenylspiro[isobenzofuran-1,4'-piperidine]

To a cold (20°) stirred solution of 30 g. of 0-bromobenzhydrol, 85 ml. of anhydrous tetrahydrofuran, and 21 ml. of hexane is added during 1.25 hours 131 ml. of 2.0 M n-butyllithium in hexane. After 3 hours, a solution of 14.8 g. of 1-methyl-4-piperidone in 50 ml. of tetrahydrofuran is added in the course of 10 minutes at −15°. The mixture is stirred at −15° for 2 hours and at room temperature for 15 hours and then treated with saturated aqueous ammonium chloride. The layers are separated, and the solid which precipitates in the organic phase is collected. Recrystallization from toluene provides colorless crystals, m.p. 190°–191°, of 4-hydroxy-4-(α-hydroxy-α-phenyl-2-tolyl)-1-methylpiperidine.

A solution of 89 g. of 4-hydroxy-4-(α-hydroxy-α-phenyl-2-tolyl)-1-methylpiperidine and 400 ml. of 88% formic acid is heated under reflux for 2 hours, cooled, diluted with water, made basic with sodium hydroxide, and extracted with chloroform. The chloroform solution is dried over magnesium sulfate, and concentrated to a solid. Recrystallization from hexane gives colorless crystals, m.p. 123°–124°, of 1,3-dihydro-1'-methyl-3-phenylspiro[isobenzofuran-1,4'-piperidine].

EXAMPLES 24–43

TABLE I

| Ex | R | m | X | $R_1$ | n | n' | $R_2$ | Y | m.p.°C |
|---|---|---|---|---|---|---|---|---|---|
| 1 | H | — | Br | $CH_3$ | 2 | 2 | Ph | OH | 182–3 |
| 2 | H | — | Br | $CH_3$ | 2 | 2 | Ph | H | 123–4 |
| 3 | H | — | Br | $CH_2Ph$ | 2 | 2 | Ph | OH | 87–90 |
| 4 | H | — | Br | $CH_2Ph$ | 2 | 2 | Ph | H | 135–7 |
| 5 | H | — | Br | $CH_2CH_2Ph$ | 2 | 2 | Ph | OH | 146–150 |
| 6 | H | — | Br | $CH_2CH_2Ph$ | 2 | 2 | Ph | H | 257–61 |
| 7 | 5-$CH_3O$ | 1 | Br | $CH_3$ | 2 | 2 | Ph | OH | 208–10 |
| 8 | 5-$CH_3O$ | 1 | Br | $CH_3$ | 2 | 2 | Ph | H | 78–80 |
| 9 | 6-$CF_3$ | 1 | Br | $CH_3$ | 2 | 2 | Ph | OH | |
| 10 | 6-$CF_3$ | 1 | Br | $CH_3$ | 2 | 2 | Ph | H | |
| 11 | H | — | Br | $CH_3$ | 2 | 2 | Ph—p$OCH_3$ | OH | 123–4 |
| 12 | H | — | Br | $CH_3$ | 2 | 2 | Ph—p$OCH_3$ | H | 127–8 |
| 13 | H | — | Br | $CH_2Ph$ | 2 | 2 | Ph—pF | OH | 60;.HCl,178 |
| 14 | H | — | Br | $CH_2Ph$ | 2 | 2 | Ph—pF | H | oil; .HCl, 235–7 |
| 15 | 5-$CH_3O$ | 1 | Br | $CH_2Ph$ | 2 | 2 | Ph—pF | OH | 70 |
| 16 | 5-$CH_3O$ | 1 | Br | $CH_2Ph$ | 2 | 2 | Ph—pF | H | oil |
| 17 | H | — | Br | $CH_3$ | 2 | 2 | $CH_3$ | OH | 157–8 |
| 18 | H | — | Br | $CH_3$ | 2 | 2 | $CH_3$ | H | .oxalate 165–6 |
| 19 | H | — | Br | $CH_2Ph$ | 2 | 2 | $CH_3$ | OH | 126–27 |
| 20 | H | — | Br | $CH_2Ph$ | 2 | 2 | $CH_3$ | H | 74–6 |
| 21 | H | — | Br | $CH_2Ph$ | 3 | 1 | Ph | OH | oil |
| 22 | H | — | Br | $CH_2Ph$ | 3 | 1 | Ph | H | 82–4 |

The compositions and structures of the compounds XII of Example 23 and of the compounds XII of Examples 24 to 43 prepared in the same manner, as well as the compositions and structures of the starting materials X and of the intermediates XI are indicated in Table II and shown in the attached drawing:

TABLE II

| Ex | R | m | X | $R_1$ | n | n' | $R_2$ | Y | m.p.°C |
|---|---|---|---|---|---|---|---|---|---|
| 23 | H | — | Br | $CH_3$ | 2 | 2 | Ph | H | 123–4 |
| 24 | 5-$CH_3O$ | — | Br | $CH_3$ | 2 | 2 | Ph | H | 78–80 |
| 25 | 6-$CH_3O$ | 1 | Br | $CH_3$ | 2 | 2 | Ph | H | 82–5 |
| 26 | 5-Cl | 1 | Br | $CH_3$ | 2 | 2 | Ph | H | |
| 27 | 6-$CH_3$ | 1 | Br | $CH_3$ | 2 | 2 | Ph | H | |
| 28 | 5,6-$OCH_2O$ | 1 | Br | $CH_3$ | 2 | 2 | Ph | H | |
| 29 | 5,6-$(CH_3O)_2$ | 2 | Br | $CH_3$ | 2 | 2 | Ph | H | 165–168 |
| 30 | H | — | Br | $CH_3$ | 2 | 2 | Ph—p$OCH_3$ | H | 127–8 |
| 31 | H | — | Br | $CH_3$ | 2 | 2 | Ph—pCl | H | |
| 32 | H | — | Br | $CH_3$ | 2 | 2 | Ph—p$CF_3$ | H | |

TABLE II-continued

| Ex | R | m | X | R₁ | n | n' | R₂ | Y | m.p.°C |
|----|---|---|----|----|---|----|----|---|--------|
| 33 | 6-F | 1 | Br | CH₃ | 2 | 2 | Ph | H | |
| 34 | 6-F | 1 | Br | CH₃ | 2 | 2 | Ph—pF | H | 134–135 |
| 35 | H | — | Br | CH₃ | 2 | 2 | Ph—pF | H | 126-7 |
| 36 | H | 1 | Br | CH₃ | 2 | 1 | Ph | H | 112–13 |
| 37 | H | 1 | Br | CH₂Ph | 3 | 2 | Ph | H | |
| 38 | H | 1 | Br | CH₃ | 2 | 2 | CH₃ | CH₃ | .HCl 250–258, dec. |
| 39 | H | 1 | Br | CH₃ | 2 | 2 | (methylenedioxyphenyl) | H | |
| 40 | H | 1 | Br | CH₃ | 2 | 2 | Ph—m,p(CH₃O)₂ | H | 67–71 |
| 41 | H | — | Br | CH₃ | 2 | 2 | Ph—pCH₃ | H | 135–136 |
| 42 | H | — | Br | CH₂Ph | 3 | 1 | Ph | H | 82–84 |
| 43 | H | — | Br | CH₃ | 2 | 2 | Ph—mF | H | 81–84 |

TABLE II - STARTING MATERIALS

Friedel-Crafts acylation of m-bromoanisole with benzoyl chloride and p-fluorobenzoyl chloride provides 2-bromo-4-methoxybenzophenone, m.p. 83°–84°, and 2-bromo-4'-fluoro-4-methoxybenzophenone, m.p. 79°–81°, respectively, which are reduced with sodium borohydride to 2-bromo-4-methoxybenzhydrol, b.p. 160° (0.05 mm.), and 2-bromo-4'-fluoro-4-methoxybenzhydrol, a liquid. Acylation of benzene with 2-bromo-5-chlorobenzoyl chloride, 2-bromo-4,5-methylene dioxybenzoyl chloride, and 2-bromo-4,5-dimethoxybenzoyl chloride provides 2-bromo-5-chlorobenzophenone, 2-bromo-4,5-methylene-dioxybenzophenone, and 2-bromo-4,5-dimethoxybenzophenone, m.p. 76°–77°, which are reduced with sodium borohydride to 2-bromo-5-chlorobenzhydrol, 2-bromo-4,5-methylenedioxybenzhydrol, and 2-bromo-4,5dimethoxybenzhydrol, m.p. 83°–85°. Acylation of anisole with 2-bromobenzoyl chloride provides 2-bromo-4'-methoxybenzophenone, m.p. 93°–95°, which is reduced to 2-bromo-4'-methoxybenzhydrol, m.p. 64°–65°. Reaction of 2-bromo-4-methylbenzaldehyde and phenylmagnesium bromide provides 2-bromo-4-methylbenzhydrol.

Addition of o-tolymagnesium bromide, p-chlorophenyl-magnesium bromide, p-trifluoromethylphenylmagnesium bromide, 3,4-methylenedioxyphenyllithium, 3,4-dimethoxyphenyllithium, p-tolylmagnesium bromide, m-fluorophenylmagnesium bromide, and p-fluorophenylmagnesium bromide to 2-bromobenzaldehyde provide, respectively, 2-bromo-2'-methylbenzhydrol; 2-bromo-4'-chlorobenzhydrol; 2-bromo-4'-trifluoromethylbenzhydrol, b.p. 125° (0.2 mm.), 2-bromo-3',4'-methylenedioxybenzhydrol; 2-bromo-3',4'-dimethyoxybenzhydrol; 2-bromo-4'-methylbenzhydrol, b.p. 145° (0.25 mm.); 2-bromo-3'-fluorobenzhydrol; 2-bromo-4'-fluorobenzhydrol, m.p. 77°–79°. Also the addition of p-fluorophenylmagnesium bromide to 2-bromo-4-fluorobenzaldehyde provides 2-bromo-4,4'-difluorobenzhydrol, m.p. 78°–80°. The 2-bromo-4-fluorobenzaldehyde is prepared by chromium trioxide oxidation of 2-bromo-4-fluorotoluene followed by hydrolysis of the intermediate acetal diacetate.

Friedel-Crafts acylation of 3-bromofluorobenzene with benzoyl chloride or p-fluorobenzoyl chloride provide, respectively, 2-bromo-4-fluorobenzophenone, b.p. 111°–114° (0.05 mm.), and 2-bromo-4,4'-difluorobenzophenone. These are reduced to 2-bromo-4-fluorobenzhydrol and 2-bromo-4,4'-difluorobenzhydrol, m.p. 78°–80°.

Addition of methyllithium to 2-bromobenzophenone provides 2-bromophenyl methyl phenyl carbinol. Addition of methyl magnesium iodide to methyl o-bromobenzoate provides 2-bromophenyl dimethyl carbinol.

EXAMPLE 44
1,3-Dihydro-1'-methyl-3-phenylspiro[isobenzofuran-1,4'-piperidine]

A solution of 152 g. of 2-bromobenzhydrol, 1 liter of methanol, and 45 ml. of conc. hydrochloric acid is heated under reflux for 24 hours, cooled, stirred with 100 g. of potassium carbonate, filtered, and distilled to provide 2-bromobenzhydryl methyl ether, b.p. 126°–128° (0.7 mm.).

To a cold (−60°) stirred solution of 2-bromobenzhydryl methyl ether in 38 ml. of tetrahydrofuran and 14 ml. of hexane is slowly added 53 ml. of 2.1 M n-butyllithium in hexane. After 2 hours, a solution of 10.7 g. of 1-methyl-4-piperidone in 15 ml. of tetrahydrofuran is added dropwise, and the suspension is stirred at −60° for 3 hours and at room temperature for 15 hours. Ice and water are added and the mixture is extracted with chloroform. The chloroform solution is dried over sodium sulfate and concentrated to a mixture of 4-hydroxy-4-(α-methoxy-α-phenyl-2-tolyl)-1-methyl-piperidine and benzhydrol methyl ether. This oil is heated under reflux for 30 minutes if 240 ml. of acetic acid containing 60 ml. of hydrochloric acid. Dilution with water and addition of excess sodium hydroxide effects precipitation of a solid. Recrystallization from hexane provides 1,3-dihydro-1'-methyl-3-phenylspiro[isobenzofuran-1,4'-piperidine], m.p. 123°–124°.

EXAMPLE 45
1'-Benzyl-1,3-dihydro-3-phenylspiro[isobenzofuran-1,3'-pyrrolidine]

By following the manipulative procedure described above in Example 44, substituting N-benzyl-3-pyrrolidone for 1-methyl-4-piperidone gives a pale yellow oil which crystallizes on standing to give rhombic crystals, m.p. 85°–87°, from low boiling petroleum ether.

Analysis: Calc. for C₂₄H₂₃NO: C 84.41%; H 6.78%; N 4.10%; Found : C 84.15%; H 6.91%; N 4.13%.

EXAMPLE 46
1'-Benzyl-1,3-dihydro-3-p-tolyspiro[isobenzofuran-1,4'-piperidine]

A. 2-Bromo-4'-methylbenzhydrol is treated according to the manipulative procedure described above in Example 44 to give 2-bromo-4'-methylbenzhydryl methyl ether, b.p. 125° (0.25 mm.). B. By following the manipulative procedure described above in Example 45, 2-bromo-4'-methylbenzhydryl methyl ether and 1-benzyl-4-piperidone are reacted to produce a white powder, m.p. 98°–99°, from isopropanol.

Analysis: Calc. for $C_{26}H_{27}NO$: C 84.51% H 7.37%; N 3.79%; Found : C 84.72%; H 7.50%; N 3.79%.

EXAMPLE 47

1'-Benzyl-1,3-dihydro-3-p-fluorophenyl-6-methoxyspiro[isobenzofuran-1,4'-piperidine]

A. 2-Bromo-4'-fluoro-4-methoxybenzhydrol is treated according to the manipulative procedure described above in Example 44 to give 2-bromo-4'-fluoro-4-methoxybenahydryl methyl ether as an oil.

B. By following the manipulative procedure described above in Example 45, 2-bromo-4'-fluoro-4-methoxybenzhydryl methyl ether and 1-benzyl-4-piperidone are reacted to produce a white solid, m.p. 86°–88°, form heptane.

Analysis: Calc. for $C_{26}H_{26}FNO_2$: C 77.39%; H 6.50%; N 3.47%; Found : C 76.84%; H 6.54%; N 3.46%.

EXAMPLE 48

1'-Benzyl-1,3-dihydro-6-fluoro-3-p-fluorophenylspiro[isobenzofuran-1,4'-piperidine]

A. 2-Bromo-4,4'-difluorobenzyhdrol is treated according to the manipulative procedure described above in Example 44, to give 2-bromo-4,4'-difluorobenzhydryl methyl ether, b.p. 105° (0.05 mm.).

B. By following the manipulative procedure described above in Example 45, 2-bromo-4,4'-difluorobenzhydryl methyl ether and 1-benzyl-4-piperidone are reacted to produce an oil.

EXAMPLE 49

1,3-Dihydro-1'-ethoxycarbonyl-3-phenylspiro[isobenzofuran1,4'-piperidine]

A solution of 7.7 g. of 1'-benzyl-1,3-dihydro-3-phenylspiro[isobenzofuran-1,4'-piperidine] (Example 4), 40 ml. of benzene and 2.5 ml. of ethyl chloroformate is heated under reflux for 18 hours and concentrated to a solid. Recrystallization from cyclohexane provides colorless crystals, m.p. 115°–119°.

Analysis: Calc. for $C_{21}H_{23}NO_3$: C 74.75%; H 6.87%; N 4.15%; Found : C 74.55%; H 7.00%; N 4.06%.

The compositions and structures of the compounds IX of Examples 50 through 64, tabulated below, are prepared in an analogous manner.

TABLE III

|  | $R_m$ | $R_2$ | $R_1$ | n,n' | Starting Material | m.p.°C |
| --- | --- | --- | --- | --- | --- | --- |
| Example 50 | H | $CH_3$ | $COOC_2H_5$ | 2,2 | Example 20 | 68–70 |
| Example 51 | H | Ph—pF | $COOC_2H_5$ | 2,2 | Example 14 | 104–106 |
| Example 52 | H | Ph | COOPh | 2,2 | Example 2 | 179–183 |
| Example 53 | H | Ph | $COOC_2H_5$ | 2,1 | Example 36 | oil |
| Example 54 | H | Ph | $COOC_2H_5$ | 3,1 | Example 22 | 115–118 |
| Example 55 | H | Ph—pCH$_3$O | $COOC_2H_5$ | 2,2 | Example 30 | 113–115 |
| Example 56 | H | Ph | $COOC_2H_5$ | 3,2 | Example 37 | oil |
| Example 57 | 6-F | Ph | $COOC_2H_5$ | 2,2 | Example 33 |  |
| Example 58 | 6-CH$_3$O | Ph | $COOC_2H_5$ | 2,2 | Example 25 | 178–180 |
| Example 59 | 5-CH$_3$O | Ph | $COOC_6H_5$ | 2,2 | Example 24 | 181–185 |
| Example 60 | 5-CH$_3$O | Ph—pF | $COOC_2H_5$ | 2,2 | Example 16 | oil |
| Example 61 | H | Ph—pCH$_3$ | $COOC_2H_5$ | 2,2 | Example 46 | 106–108 |
| Example 62 | 6-CH$_3$O | Ph—pF | $COOC_2H_5$ | 2,2 | Example 47 | 168–170 |
| Example 63 | 6-F | Ph—pF | $COOC_2H_5$ | 2,2 | Example 48 | 123–126 |
| Example 64 | H | Ph—m,p(CH$_3$O)$_2$ | COOPh | 2,2 | Example 40 | 170–172 |

EXAMPLE 65

1,3-Dihydro-3-phenylspiro[isobenzofuran-1,4'-piperidine]

A. A solution of 6.3 g. of 1,3-dihydro-1'-ethoxycarbonyl-3-phenylspiro[isobenzofuran-1,4'-piperidine] (Example 49), 300 ml. of ethanol, and 240 ml. of 20% aqueous potassium hydroxide is heated under reflux for 9 hours, cooled, concentrated to 250 ml., diluted with water, and extracted with chloroform. The chloroform solution is dried over potassium carbonate and concentrated. The residue is recrystallized from cyclohexane to provide colorless crystals, m.p. 119°–123°.

Analysis: Calc. for $C_{18}H_{19}NO$: C 81.48%; H 7.22%; N 5.28%; Found : C 81.55%; H 7.56%; N 5.12%. Hydrochloride salt, m.p. 262°.

B. A mixture of 2.9 G. of 1'-benzyl-1,3-dihydro-3-phenylspiro[phenylspiro[isobenzofuran-1,4'-piperidine], (Example 4), 0.4 g. of 10% palladium on carbon, 20 ml. of 95% ethanol, and 2 ml. of conc. hydrochloric acid is hydrogenated at 50 p.s.i. and 50°. After hydrogen uptake ceases, the mixture is filtered and the filtrate concentrated. Recrystallization of the residue from cyclohexane provides colorless crystals, m.p. 119°–123°.

The compositions and structures of the compounds XIII of Examples 66 through 79, tabulated below, are prepared in analogous manner.

TABLE IV

|  | $R_m$ | $R_2$ | Y | n,n' | Starting Material | m.p.°C |
| --- | --- | --- | --- | --- | --- | --- |
| Example 66 | H | $CH_3$ | H | 2,2 | Example 50 | .HCl, 183–184 |
| Example 67 | H | Ph—pF | H | 2,2 | Example 51 | 98–100 |
| Example 68 | H | Ph | H | 2,1 | Example 53 | 90–95 |
| Example 69 | H | Ph | H | 3,1 | Example 54 | 106–110 |
| Example 70 | H | Ph—pCH$_3$O | H | 2,2 | Example 55 | 101–103 |
| Example 71 | H | Ph | H | 3,2 | Example 56 | .HCl>250 |

TABLE IV-continued

|  | $R_m$ | $R_2$ | Y | n,n' | Starting Material | m.p.°C |
|---|---|---|---|---|---|---|
| Example 72 | 6-F | Ph | H | 2,2 | Example 57 | |
| Example 73 | 6-CH₃O | Ph | H | 2,2 | Example 58 | .HCl, 204–212 |
| Example 74 | 5-CH₃O | Ph | H | 2,2 | Example 59 | .HCl, 265–268 |
| Example 75 | 5-CH₃O | Ph—pF | H | 2,2 | Example 60 | .HCl, 275 |
| Example 76 | H | Ph—pCH₃ | H | 2,2 | Example 61 | 116–117 |
| Example 77 | 6-F | Ph—pF | H | 2,2 | Example 63 | 111–112 |
| Example 78 | H | Ph | OH | 2,2 | Example 3 | 183–184 |
| Example 79 | H | Ph—m,p(CH₃O)₂ | H | 2,2 | Example 64 | .HCl, 212–218 |

EXAMPLE 80

1'-Acetyl-1,3-dihydro-3-phenylspiro[isobenzofuran-1,4'-piperdine]

To a cold stirred solution of 6.0 g. of 1,3-dihydro-3-phenylspiro[isobenzofuran-1,4'-piperidine] (Example 65), 2.4 g. of triethylamine, and 50 ml. of chloroform is added dropwise a solution of 2.0 g. of acetyl chloride and 50 ml. of chloroform. The mixture is stirred for 2 hours at room temperature, washed with water, dried over sodium sulfate, and concentrated. The residue is recrystallized from chloroform to provide colorless crystals, m.p. 128°–130°.

Analysis: Calc. for $C_{20}H_{21}NO_2$: C 77.89%; H 6.90%; 4.55%; Found : C 78.06%; H 6.99%; N 4.43%.

The compositions and structures of the compounds IX of Examples 81 through 88, tabulated below, are prepared in analogous manner.

EXAMPLE 89

1,3-Dihydro-1'-ethyl-3-phenylspiro[isobenzofuran-1,4'piperidine]

To a stirred suspension of 0.53 g. of lithium aluminum hydride in 50 ml. of tetrahydrofuran is added dropwise a solution of 2.20 g. of 1'-acetyl-1,3-dihydro-3-phenylspiro[isobenzofuran-1,4'-piperidine] (Example 80), in 50 ml. of tetrahydrofuran. The mixture is heated under reflux for 2 hours, cooled, quenched cautiously with water, and extracted with ether. The ether solution is dried over sodium sulfate and concentrated to a solid. Recrystallization from chloroform provides colorless crystals, m.p. 113°–115°.

Analysis: Calc. for $C_{20}H_{23}HO$: C 81.87%; H 7.91%; N 4.77%; Found : C 81.76%; H 8.10%; N 4.62%.

The compositions and structures of the compounds IX of Examples 90 through 98, tabulated below, are prepared in analogous manner.

TABLE V

|  | $R_m$ | $R_2$ | $R_1$ | n,n' | Starting Material | m.p.°C |
|---|---|---|---|---|---|---|
| Example 81 | H | Ph | COC₂H₅ | 2,2 | Example 65 | 116–119 |
| Example 82 | H | Ph | COC₃H₇ | 2,2 | Example 65 | 110–112 |
| Example 83 | H | Ph | COCH₂Ph | 2,2 | Example 65 | 174–176 |
| Example 84 | H | Ph | COPhCH₃ | 2,2 | Example 65 | 172–175 |
| Example 85 | H | Ph | CO-◁ | 2,2 | Example 65 | 133–135 |
| Example 86 | H | Ph—pF | CO-◁ | 2,2 | Example 67 | 149–152 |
| Example 87 | H | Ph | CO-◇ | 2,2 | Example 65 | 127–130 |
| Example 88 | H | Ph | CO-◁ | 3,2 | Example 71 | oil |

TABLE VI

|  | $R_m$ | $R_2$ | $R_1$ | n,n' | Starting Material | m.p.°C |
|---|---|---|---|---|---|---|
| Example 90 | H | Ph | C₃H₇ | 2,2 | Example 81 | 98–100 |
| Example 91 | H | Ph | C₄H₉ | 2,2 | Example 82 | 102–103 |
| Example 92 | H | Ph | CH₂-◁ | 2,2 | Example 85 | 97–99 |
| Example 93 | H | Ph—pF | CH₂-◁ | 2,2 | Example 86 | .HBr, 233–235 |
| Example 94 | H | Ph | CH₂-◇ | 2,2 | Example 89 | 119–121 |
| Example 95 | H | Ph | CH₂-◁ | 3,2 | Example 88 | .HCl, 203–206 |
| Example 96 | H | Ph—pCH₃ | CH₃ | 2,2 | Example 61 | 135–136 |
| Example 97 | H | Ph | CH₃ | 3,2 | Example 56 | 88–89 |

TABLE VI-continued

|  | $R_m$ | $R_2$ | $R_1$ | n,n' | Starting Material | m.p.°C |
|---|---|---|---|---|---|---|
| Example 98 | 6-CH$_3$O | Ph—pF | CH$_3$ | 2,2 | Example 62 | .HBr, 235 dec. |

EXAMPLE 99

1,3-Dihydro-1'-[3-(p-fluorobenzoyl)propyl]-3-phenyl-spiro[isobenzofuran-1,4'-piperidine]

A stirred mixture of 4.9 g. of 1.3-dihydro-3-phenyl-spiro[isobenzofuran-1,4'-piperidine] (Example 65), 4.9 g. of ω-chloro-p-fluorobutyrophenone ethylene ketal, 10 g. of potassium carbonate, and 50 ml. of butanol is heated under reflux for 46 hours and filtered. The filtrate is concentrated to an oil, which is stirred with 50 ml. of 3N hydrochloric acid and 50 ml. of ethanol. The mixture is made basic with sodium hydroxide and extracted with benzene. The benzene solution is dried over sodium sulfate and concentrated. The residue is recrystallized from ether to provide colorless crystals, m.p. 137°–138°.

Analysis: Calc. for C$_{28}$H$_{28}$FNO$_2$: C 78.30%; H 6.57%; N 3.26%; Found : C 78.28%; H 6.59%; N 3.12%.

The compositions and structures of compounds IX of Examples 100 through 111, tabulated below, are prepared in analogous manner. The acid hydrolysis step of Example 99 is omitted when the alkylating agent does not contain a ketal group.

solid. Recrystallization from acetone-water provides colorless crystals, m.p. 129°–133°.

Analysis: Calc. for C$_{27}$H$_{29}$NO$_3$: C 78.03%; H 7.05%; N 3.37%; Found: C 78.15%; H 7.12%; N 3.23%.

EXAMPLE 113

1,3-Dihydro-3-(4-hydroxyphenyl)-1'-methyl-spiro[isobenzofuran-1,4'-piperidine]

A solution of 3.5 g. of 1,3-dihydro-3-(4-methoxyphenyl)-1'-methylspiro[isobenzofuran-1,4'-piperidine], (Example 12), and 20 ml. of 48% hydrobromic acid is heated under reflux, cooled, diluted with water, neutralized with sodium bicarbonate, and extracted with chloroform. The chloroform solution is dried over magnesium sulfate and concentrated to an oil. Trituration with ether provides crystals, m.p. 132°dec. Recrystallization raises the melting point to 273°dec.

EXAMPLE 114

1,3-Dihydro-6-hydroxy-1'-methyl-3-phenyl-spiro[isobenzofuran-1,4'-piperidine]

By following the manipulative procedure described above in example 113, 1,3-dihydro-6-methoxy-1'-methyl-3-phenylspiro[isobenzofuran-1,4'-piperidine], (Example 25), gives a faintly pink solid, m.p. 207°–212°.

Analysis: Calc. for C$_{19}$H$_{21}$NO$_2$: C 77.25%, H 7.18%; N 4.74%; Found: C 77.05%; H 7.23%; N 4.74%.

EXAMPLE 115

1,3-Dihydro-5-hydroxy-1'-methyl-3-phenyl-spiro[isobenzofuran-1,4'-piperidine]

By following the manipulative procedure described above in Example 113, 1,3-dihydro-5-methoxy-1'-methyl-3-phenylspiro[isobenzofuran-1,4'-piperidine],

TABLE VII

| Ex. | $R_m$ | $R_2$ | $R_1$ | n,n' | m.p.°C | Starting Material Ex. | Alkylating Agent |
|---|---|---|---|---|---|---|---|
| 100 | H | CH$_3$ | —(CH$_2$)$_3$CO—PhF | 2,2 |  | 66 | Cl(CH$_2$)$_3$—C(—PhF)(OCH$_2$CH$_2$O) |
| 101 | H | Ph | —(CH$_2$)$_3$CO—PhF | 2,1 |  | 68 | Cl(CH$_2$)$_3$—C(—PhF)(OCH$_2$CH$_2$O) |
| 102 | H | Ph | —(CH$_2$)$_3$CH—(PhF)$_2$ | 2,2 | .HCl, 185–190 | 65 | Cl(CH$_2$)$_3$CH—(PhF)$_2$ |
| 103 | H | CH$_3$ | —(CH$_2$)$_3$CH—(PhF)$_2$ | 2,2 | 167–170 | 66 | Cl(CH$_2$)$_3$CH—(PhF)$_2$ |
| 104 | H | Ph | —CH$_2$CH=C(CH$_3$)$_2$ | 2,2 | 119–121 | 65 | BrCH$_2$CH=C(CH$_3$)$_2$ |
| 105 | H | Ph | —CH$_2$CH=CH$_2$ | 2,2 | 129–131 | 65 | BrCH$_2$CH=CH$_2$ |
| 106 | H | Ph | —CH$_2$CH$_2$O—CH—Ph$_2$ | 2,2 | oil | 65 | ClCH$_2$CH$_2$OCH—Ph$_2$ |
| 107 | H | Ph | —CH$_2$CH$_2$CO—Ph | 2,2 |  | 65 | (CH$_3$)$_3$N$^+$CH$_2$CH$_2$CO—Ph |
| 108 | H | Ph | i-C$_3$H$_7$ | 2,2 | 121–124 | 65 | CH$_3$CHICH$_3$ |
| 109 | H | Ph | (CH$_2$)$_3$—Ph | 2,2 | 89–92 | 65 | Br(CH$_2$)$_3$Ph |
| 110 | H | Ph | CH$_2$CH=CHPh | 2,2 | 142–144 | 65 | BrCH$_2$CH=CHPh |
| 111 | H | CH$_3$ | CH$_2$-cyclopropyl | 2,2 | 196–199 | 66 | BrCH$_2$-cyclopropyl |

EXAMPLE 112

1'-Benzyl-1,3-dihydro-3,5-dimethoxy-3-phenyl-spiro[isobenzofuran-1,4'-piperidine]

A solution of 1'-benzyl-1,3-dihydro-3-hydroxy-5-methoxy-3-phenylspiro[isobenzofuran-1,4'-piperidine] (prepared by method of Example 1), methanol, and a catalytic amount of methanolic hydrogen chloride is heated under reflux, cooled, made basic with sodium hydroxide, and diluted with water. The mixture is extracted with ethyl acetate, and the ethyl acetate solution is dried over sodium sulfate and concentrated to a (Example 24), gives a cream colored solid, m.p. 193°–200°.

Analysis: Calc. for $C_{19}H_{21}NO_2$: C 77.25%; H 7.18%; N 4.74%; Found: C 77.00%; H 7.40%; N 4.66%.

EXAMPLE 116

1,3-Dihydro-6-hydroxy-3-phenylspiro[isobenzofuran-1,4'-piperidine]

A suspension of 2.0 g. of 1,3-dihydro-6-methoxy-3-phenylspiro[isobenzofuran-1,4'-piperidine], (Example 73), and 32 ml. of a 48% hydrobromic acid solution is heated at reflux, effecting the separation of a hydrobromide salt as a crystalline precipitate. The mixture is poured into ice-water with stirring, the precipitate collected by filtration, the filter cake washed with water, and dried. Recrystallization from ethanol gives colorless crystals, m.p. 274°–276°, dec.

Analysis: Calc. for $C_{18}H_{19}NO_2.HBr$: C 59.67%; H 5.58%; N 3.87% Br 22.06%; Found: C 59.83%; H 5.64%; N 3.95% Br 21.86%.

EXAMPLE 117

1,3-Dihydro-1'-(3-hydroxy-3-phenylpropyl)-3-phenylspiro[isobenzofuran-1,4'-piperidine]

A solution of 2.5 g. of 1'-(2-benzoylethyl)-1,3-dihydro-3-phenylspiro[isobenzofuran-1,4'-piperidine], (Example 107), 30 ml. of methanol, and 0.35 g. of sodium borohydride is stirred at room temperature for 4 hours, diluted with water, and extracted with chloroform. The chloroform solution is dried over sodium sulfate and concentrated to provide 1,3-dihydro-1'-(3-hydroxy-3-phenylpropyl)-3-phenylspiro[isobenzofuran-1,4'-piperidine].

EXAMPLE 118

1,3-Dihydro-1'-[4-p-fluorophenyl)-3-hydroxybutyl]-3-phenylspiro[isobenzofuran-1,4'-piperidine]

By following the manipulative procedure described above in Example 117, 1,3-dihydro-1'-[3-(p-fluorobenzoly)propyl]-3-phenylspiro[isobenzofuran-1,4'-piperidine], (Example 99), produces a yellow oil. The oil is triturated with an ether-petroleum ether mixture to give white crystals which are recrystallized from ethanol to give a white crystalline solid, m.p. 151°–154°.

Analysis: Calc. for $C_{28}H_{30}FNO_2$: C 77.93%; H 7.01%; N 3.25%; Found: C 77.78%; H 7.07%; N 3.19%.

EXAMPLE 119

1,3-Dihydro-3-p-hydroxyphenyl-1'-methylspiro[isobenzofuran-1,4'-piperidine]

A mixture of 1.0 g. of 1,3-dihydro-3-p-methoxyphenyl-1'-methylspiro[isobenzofuran-1,4'-piperidine] (Example 12), 1.0 g. of a 57% sodium hydride dispersion, and dimethylformamide is stirred under nitrogen. To the stirring mixture is rapidly added 2.0 ml. of ethanethiol. The mixture is refluxed under nitrogen for 4 hours, cooled, poured into ice-water, and acidified with 1N hydrochloric acid. The product is collected, dried, and dissolved in boiling dimethyl sulfoxide, and the solution is filtered. Upon cooling small colorless crystals, m.p. 273° dec., separate.

Analysis: Calc. for $C_{19}H_{21}NO_2$: C 77.26%; H 7.17%; N 4.74%; Found: C 76.28%; H 7.33%; N 4.71%.

EXAMPLE 120

1'-Benzyl-1,3-dihydro-3,3-diphenylspiro[isobenzofuran-1,3'-piperidine]

Reaction of 1'-benzyl-1,3-dihydrospiro[isobenzofuran-1,3'-piperidine]-3-one with a large excess of phenyllithium by the method described in Example 1 provides off-white crystals, m.p. 144°–146°.

Analysis: Calc. for $C_{31}H_{29}NO$: C 86.27%; H 6.77%; N 3.25%; Found: C 86.22%; H 7.09%; N 3.21%.

EXAMPLE 121

(−)-1,3-Dihydro-3-phenylspiro[isobenzofuran-1,4'-piperidine]

To a stirred solution of 0.80 g. of 1,3-dihydro-3-phenylspiro[isobenzofuran-1,4'-piperidine], (Example 65), and 3 ml. of methanol is added a solution of 1.16 g. of di-(p-toluoyl)-d-tartaric acid in 6 ml. of methanol. The solution is concentrated to dryness, and the residue is recrystallized three times from methanol-water to provide colorless crystals. The crystals are dissolved in methanol and treated with an excess of aqueous sodium hydroxide. The mixture is extracted with ether, and the ether solution is dried over sodium sulfate and concentrated to an oily solid. Recrystallization from cyclohexane provides off-white crystals, m.p. 99°–107°, $[\alpha]_D^{25°} = 126.0°$ (c=1.35, MeOH).

EXAMPLE 122

(+)-1,3-Dihydro-3-phenylspiro]isobenzofuran-1,4'-piperidine]

The compound, colorless crystals, m.p. 104°–112°, $[\alpha]_D^{25°} = +134.4°$ (c=1.35, MeOH), is prepared from 1,3-dihydro-3-phenylspiro[isobenzofuran-1,4'-piperidine], (Example 65), and di-(p-toluoyl)-1-tartaric acid by the method described in Example 121, or is alternatively recovered from the aqueous-methanolic mother liquors of Example 121.

EXAMPLE 123

1,3-Dihydro-1',3-dimethyl-3-phenylspiro[isobenzofuran-1,4'-piperidine]

A solution of 1.4 g. of 1,3-dihydro-1'-methyl-3-phenylspiro[isobenzofuran-1,4'-piperidine], (Example 2), in 20 ml. of tetrahydrofuran is cooled to −50° and treated dropwise with 4 ml. of butyllithium in hexane. Stirring is continued for 30 minutes under nitrogen. To the solution is slowly added 900 mg. of dimethylsulfate in 10 ml. of tetrahydrofuran. The mixture is stirred at −10° for 1 hour and overnight at ambient temperature. Ice is added, the mixture is extracted with ether, and the organic solution is concentrated to an oil. The oil is converted to the hydrobromide salt and recrystallized from ethyl acetate to give crystals, m.p. 122°–125°.

Analysis: Calc. for $C_{20}H_{23}NO.HBr$: C 64.17%; H, 6.46%; N 3.74%; Br 21.35%; Found: C 64.27%; H 6.68%; N 3.42%; Br 20.98%.

The compositions and structures of compounds XII of Examples 124 through 126, tabulated below, are prepared from 1,3-dihydro-1'-methyl-3-phenylspiro[isobenzofuran-1,4'-piperidine], (Example 2), in analogous manner.

TABLE IX

| Ex. | $R_m$ | $R_2$ | Y | $R_1$ | n,n' | m.p.°C | Alkylating Agent |
|---|---|---|---|---|---|---|---|
| 124 | H | Ph | $C_2H_5$ | $CH_3$ | 2,2 | 107–108 | $BrCH_2CH_3$ |
| 125 | H | Ph | n-$C_3H_7$ | $CH_3$ | 2,2 | 205–206,dec. | $BrCH_2CH_2CH_3$ |
| 126 | H | Ph | n-$C_4H_9$ | $CH_3$ | 2,2 | 203–204,dec. | $BrCH_2CH_2CH_2CH_3$ |

EXAMPLE 127

1'-Cyclopropylmethyl-1,3-dihydro-3-phenyl-spiro[isobenzofuran-1,3'-pyrrolidine]

Reaction of 1,3-dihydro-3-phenylspiro[isobenzofuran-1,3'-pyrrolidine] with cyclopropylcarbonyl chloride by the method of Example 80, followed by lithium aluminum hydride reduction by the method of Example 89 provides an amine. The amine is converted to its hydrobromide salt, m.p. 187°–190°, from an acetone-ethyl acetate mixture.

Analysis: Calc. for $C_{21}H_{23}NO \cdot HBr$: C 65.28%; H 6.26%; N 3.62%; Found: C 65.08%; H 6.36%; N 3.45%.

We claim:

1. A compound of the formula

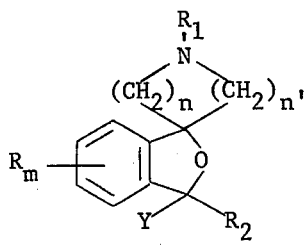

in which
R is hydrogen, alkyl of 1 to 6 carbon atoms, alkoxy of 1 to 6 carbon atoms, trifluoromethyl, halogen, hydroxy, or methylenedioxy;
$R_1$ is hydrogen, alkyl of 1 to 6 carbon atoms, cycloalkylalkyl of 4 to 8 carbon atoms, alkenyl of 3 to 6 carbon atoms, phenylalkyl of the formula $(CH_2)_x$—PhR, diphenylalkyl of the formula $(CH_2)_m$—CH(PhR)$_2$, diphenylmethoxyalkyl of the formula —$(CH_2)_m$—OCHPh$_2$, alkanoyl of 2 to 6 carbon atoms, phenylalkanoyl of the formula —CO(CH$_2)_x$—PhR, benzoyl of the formula —COPhR, benzoylalkyl of the formula —(CH$_2)_m$—COPhR, phenylhydroxyalkyl of the formula —(CH$_2)_m$CHOHPhR, alkoxycarbonyl of 2 to 6 carbon atoms, phenyloxycarbonyl, or cycloalkylcarbonyl of 4 to 8 carbon atoms;
$R_2$ is alkyl of 1 to 6 carbon atoms or phenyl of the formula PhR$_m$;
Y is hydrogen, alkyl of 1 to 6 carbon atoms, alkoxy of 1 to 6 carbon atoms, hydroxy or phenyl of the formula PhR;
Ph is phenyl;
m, n and n' are integers from 1 to 3, the sum of n and n' being from 3 to 5; and
x is an integer from 1 to 4, and
the optical antipodes and the pharmaceutically acceptable acid addition salts thereof.

2. A compound as defined in claim 1 in which
R is hydrogen, akyl of 1 to 3 carbon atoms, alkoxy of 1 to 3 carbon atoms, trifluoromethyl, fluorine, chlorine, hydroxy or methylenedioxy;
$R_1$ is hydrogen, alkyl of 1 to 6 atoms, cycloalkylalkyl of 4 or 5 carbon atoms, alkenyl of 3 to 5 carbon atoms, phenylalkyl of the formula —(CH$_2)_m$—PhR, diphenylalkyl of the formula —(CH$_2)_m$—CH(PhR)$_2$, alkanoyl of 2 to 4 carbon atoms, phenylalkanoyl of the formula —CO(CH$_2)_m$—PhR, benzoylalkyl of the formula —(CH$_2)_m$—COPhR, benzoyl of the formula —COPhR, alkoxycarbonyl of 2 or 3 carbon atoms, or cycloalkylcarbonyl of 4 to 7 carbon atoms;
$R_2$ is alkyl of 1 to 3 carbon atoms, or phenyl of the formula —PhR'', R'' being hydrogen, alkyl of 1 to 3 carbon atoms, alkoxy of 1 to 3 carbon atoms, halogen, methylenedioxy or trifluoromethyl;
Y is hydrogen, alkyl of 1 to 3 carbon atoms, alkoxy of 1 to 4 carbon atoms or phenyl of the formula —PhR'', and
Ph, m, n and n' are as defined in claim 1.

3. The compound defined in claim 1 which is 1,3-dihydro-3-phenylspiro[isobenzofuran-1,4'-piperidine] and the pharmaceutically acceptable acid addition salts thereof.

4. The compound defined in claim 1 which is 1,3-dihydro-1'-methyl-3-phenylspiro[isobenzofuran-1,4'-piperidine] and the pharmaceutically acceptable acid addition salts thereof.

5. The compound defined in claim 1 which is 1,3-dihydro-1'-cyclopropylmethyl-3-phenylspiro[isobenzofuran-1,4'-piperidine] and the pharmaceutically acceptable acid addition salts thereof.

6. The compound defined in claim 1 which is 1,3-dihydro-1'-[3-(p-fluorobenzoyl)propyl]-3-phenylspiro[isobenzofuran-1,4'-piperidine] and the pharmaceutically acceptable acid addition salts thereof.

7. The compound defined in claim 1 which is 1,3-dihydro-3-(p-fluorophenyl)spiro[isobenzofuran-1,4'-piperidine] and the pharmaceutically acceptable acid addition salts thereof.

8. The compound defined in claim 1 which is 1,3-dihydro-6-fluoro-1'-methyl-3-(p-fluorophenyl)-spiro[isobenzofuran-1,4'-piperidine] and the pharmaceutically acceptable acid addition salts thereof.

9. The compound defined in claim 1 which is 1,3-dihydro-3-phenylspiro[isobenzofuran-1,3'-pyrrolidine] and the pharmaceutically acceptable acid addition salts thereof.

10. The compound defined in claim 1 which is 1,3-dihydro-1'-methyl-3-phenylspiro[isobenzofuran-1,3'-pyrrolidine] and the pharmaceutically acceptable acid addition salts thereof.

11. The compound defined in claim 1 which is 1'-cyclopropylmethyl-1,3-dihydro-3-phenylspiro[isobenzofuran-1,3'-pyrrolidine] and the pharmaceutically acceptable acid addition salts thereof.

12. The compound defined in claim 1 which is 1,3-dihydro-3-p-tolylspiro[isobenzofuran-1,4'-piperidine] and the pharmaceutically acceptable acid addition salts thereof.

13. The compound defined in claim 1 which is 1,3-dihydro-6-fluoro-3-p-fluorophenylspiro[isobenzofuran-1,4'-piperidine] and the pharmaceutically acceptable acid addition salts thereof.

14. The compound defined in claim 1 which is 1,3-dihydro-6-methoxy-3-phenylspiro[isobenzofuran-1,4'-piperidine] and the pharmaceutically acceptable acid addition salts thereof.

15. The compound defined in claim 1 which is 1,3-dihydro-3-p-fluorophenyl-1'-methylspiro[isobenzofuran-1,4'-piperidine] and the pharmaceutically acceptable acid addition salts thereof.

16. The compound defined in claim 1 which is 1,3-dihydro-3-p-methoxyphenylspiro[isobenzofuran-1,4'-piperidine] and the pharmaceutically acceptable acid addition salts thereof.

17. Process for the preparation of a compound as defined in claim 1 which comprises reacting an o-bromobenzyl alcohol or an o-bromobenzyl alkyl ether with an alkyllithium to form the corresponding lithium o-lithiobenzyloxide or o-lithiobenzyl alkyl ether, reacting said lithium o-lithiobenzyloxide or o-lithiobenzyl alkyl ether with a cycloazalkanone to prepare the corresponding ($\alpha$-hydroxy-o-tolyl)cycloazalkanol or ($\alpha$-hydroxy-o-tolyl)cycloazalkyl alkyl ether, and treating said ($\alpha$-hydroxy-o-tolyl)cycloazalkanol or ($\alpha$-hydroxy-o-tolyl)cycloazalkyl alkyl ether with acid to effect cyclization to the corresponding 1,3-dihydrospiro[isobenzofuran-cycloazalkane].

18. A pharmaceutical composition which comprises between about 0.5 and about 70 percent by weight of a compound defined in claim 1 as an essential active ingredient, the balance being a pharmaceutically acceptable carrier therefor.

19. The compound defined in claim 1 which is 1,3-dihydro-6-hydroxy-3-phenylspiro[isobenzofuran-1,4'-piperidine] and the pharmaceutically acceptable acid addition salts thereof.

20. The compound defined in claim 1 which is 1,3-dihydro-5-hydroxy-3-phenylspiro[isobenzofuran-1,4'-piperidine] and the pharmaceutically acceptable acid addition salts thereof.

21. The compound as defined in claim 1 which is 1,3-dihydro-3-(4-hydroxyphenyl)spiro[isobenzofuran-1,4'-piperidine] and the pharmaceutically acceptable acid addition salts thereof.

22. The compound defined in claim 1 which is 1,3-dihydro-1'-ethoxycarbonyl-3-methylspiro[isobenzofuran-1,4'-piperidine] and the pharmaceutically acceptable acid addition salts thereof.

23. The compound defined in claim 1 which is 1,3-dihydro-1'-[3-(p-fluorobenzoyl)propyl]-3-methylspiro[isobenzofuran-1,4'-piperidine] and the pharmaceutically acceptable acid addition salts thereof.

24. The compound defined in claim 1 which is 1,3-dihydro-1'-[4,4-di(p-fluorophenyl)butyl]-3-methylspiro[isobenzofuran-1,4'-piperidine] and the pharmaceutically acceptable acid addition salts thereof.

25. The compound defined in claim 1 which is 1,3-dihydro-1'-cyclopropylmethyl-3-methylspiro[isobenzofuran-1,4'-piperidine] and the pharmaceutically acceptable acid addition salts thereof.

26. A method of treating depression, depressing the central nervous system or alleviating pain which comprises administering to a patient a pharmaceutically effective amount of a compound defined in claim 1.

27. The method of treating depression as defined in claim 26 in which the pharmaceutically effective compound is 1,3-dihydro-3-phenylspiro[isobenzofuran-1,4'-piperidine] or a pharmaceutically acceptable acid addition salt thereof.

28. The method of treating depression as defined in claim 26 in which the pharmaceutically effective compound is 1,3-dihydro-1'-methyl-3-phenylspiro[isobenzofuran-1,4'-piperidine] or a pharmaceutically acceptable acid addition salt thereof.

29. The method of treating depression as defined in claim 26 in which the pharmaceutically effective compound is 1,3-dihydro-1'-cyclopropylmethyl-3-phenylspiro[isobenzofuran-1,4'-piperidine] or a pharmaceutically acceptable acid addition salt thereof.

30. The method of treating depression as defined in claim 26 in which the pharmaceutically effective compound is 1,3-dihydro-3-(p-fluorophenyl)spiro[isobenzofuran-1,4'-piperidine] or a pharmaceutically acceptable acid addition salt thereof.

31. The method of treating depression as defined in claim 26 in which the pharmaceutically effective compound is 1,3-dihydro-6-fluoro-1'-methyl-3-(p-fluorophenyl)spiro[isobenzofuran-1,4'-piperidine] or a pharmaceutically acceptable acid addition salt thereof.

32. The method of treating depression as defined in claim 26 in which the pharmaceutically effective compound is 1,3-dihydro-3-phenylspiro[isobenzofuran-1,3'-pyrrolidine] or a pharmaceutically acceptable acid addition salt thereof.

33. The method of treating depression as defined in claim 26 in which the pharmaceutically effective compound is 1,3-dihydro-1'-methyl-3-phenylspiro[isobenzofuran-1,3'-pyrrolidine] or a pharmaceutically acceptable acid addition salt thereof.

34. The method of treating depression as defined in claim 26 in which the pharmaceutically effective compound is 1'-cyclopropylmethyl-1,3-dihydro-3-phenylspiro[isobenzofuran-1,3'-pyrrolidine] or a pharmaceutically acceptable acid addition salt thereof.

35. The method of treating depression as defined in claim 26 in which the pharmaceutically effective compound is 1,3-dihydro-3-p-tolylspiro[isobenzofuran-1,4'-piperidine] or a pharmaceutically acceptable acid addition salt thereof.

36. The method of treating depression as defined in claim 26 in which the pharmaceutically effective compound is 1,3-dihydro-6-fluoro-3-p-fluorophenylspiro[isobenzofuran-1,4'-piperidine] or a pharmaceutically acceptable acid addition salt thereof.

37. The method of treating depression as defined in claim 26 in which the pharmaceutically effective compound is 1,3-dihydro-6-methoxy-3-phenylspiro[isobenzofuran-1,4'-piperidine] or a pharmaceutically acceptable acid addition salt thereof.

38. The method of treating depression as defined in claim 26 in which the pharmaceutically effective compound is 1,3-dihydro-3-p-fluorophenyl-1'-methylspiro[isobenzofuran-1,4'-piperidine] or a pharmaceutically acceptable acid addition salt thereof.

39. The method of treating depression as defined in claim 26 in which the pharmaceutically effective compound is 1,3-dihydro-3-p-methoxyphenylspiro[isobenzofuran-1,4'-piperidine] or a pharmaceutically acceptable acid addition salt thereof.

40. The method of treating depression as defined in claim 26 in which the pharmaceutically effective compound is 1,3-dihydro-6-hydroxy-3-phenylspiro[isobenzofuran-1,4'-piperidine] or a pharmaceutically acceptable acid addition salt thereof.

41. The method of treating depression as defined in claim 26 in which the pharmaceutically effective compound is 1,3-dihydro-3-(4-hydroxyphenyl)-spiro[isobenzofuran-1,4'-piperidine] or a pharmaceutically acceptable acid addition salt thereof.

42. The method of depressing the central nervous system as defined in claim 26 in which the pharmaceutically effective compound is 1,3-dihydro-1'-cyclopropylmethyl-3-phenylspiro[isobenzofuran-1,4'-piperidine] or a pharmaceutically acceptable acid addition salt thereof.

43. The method of depressing the central nervous system as defined in claim 26 in which the pharmaceutically effective compound is 1,3-dihydro-1'-[3-(p-fluorobenzoyl)propyl]-3-phenylspiro[isobenzofuran-1,4'-piperidine] or a pharmaceutically acceptable acid addition salt thereof.

44. The method of depressing the central nervous system as defined in claim 26 in which the pharmaceutically effective compound is 1'-cyclopropylmethyl-1,3-dihydro-3-phenylspiro[isobenzofuran-1,3'-pyrrolidine] or a pharmaceutically acceptable acid addition salt thereof.

45. The pharmaceutical composition defined in claim 18 in which the essential active compound is 1,3-dihydro-3-phenylspiro[isobenzofuran-1,4'-piperidine] or a pharmaceutically acceptable acid addition salt thereof.

46. The pharmaceutical composition defined in claim 18 in which the essential active compound is 1,3-dihydro-1'-methyl-3-phenylspiro[isobenzofuran-1,4'-piperidine] or a pharmaceutically acceptable acid addition salt thereof.

47. The pharmaceutical composition defined in claim 18 in which the essential active compound is 1,3-dihydro-1'-[3-(p-fluorobenzoyl)propyl]-3-phenyl-spiro[isobenzofuran-1,4'-piperidine] or a pharmaceutically acceptable acid addition salt thereof.

48. The pharmaceutical composition defined in claim 18 in which the essential active compound is 1,3-dihydro-3-(p-fluorophenyl)spiro[isobenzofuran-1,4'-piperidine] or a pharmaceutically acceptable acid addition salt thereof.

* * * * *

UNITED STATES PATENT AND TRADEMARK OFFICE
CERTIFICATE OF CORRECTION

PATENT NO. : 3,959,475
DATED : May 25, 1976
INVENTOR(S) : Bauer et al.

It is certified that error appears in the above-identified patent and that said Letters Patent are hereby corrected as shown below:

Column 2, line 9, change "-PhR" to -- -$PhR_m$ --;

Column 3, lines 33 and 34, in each instance, change the first bracket "]" to --[--;

Column 6, line 55, change "1'-(4-" to --1'-[3-(4- --;

Column 6, line 63, change "phenyl)-   1'-" to --phenyl)-1'- --;

Column 10, line 5, change "(20°)" to --(-20°)--;

Column 11, lines 35 to 36, change "4,5dimethoxy" to --4,5-dimethoxy--;

Column 11, line 43, change "o-tolymagnesium" to --o-tolylmagnesium--;

Column 12, line 64, change "p-tolyspiro" to --p-tolylspiro--;

Column 13, line 30, change "fluoro-4  -methoxy" to --fluoro-4-methoxy--;

Column 13, line 33, change "benahydryl" to --benzhydryl--;

Column 14, line 44, change "G" to --g--;

Column 14, line 45, change "phenylspiro[phenylspiro[iso" to --phenylspiro[iso--;

UNITED STATES PATENT AND TRADEMARK OFFICE
CERTIFICATE OF CORRECTION

PATENT NO. : 3,959,475
DATED : May 25, 1976
INVENTOR(S) : Bauer et al.

It is certified that error appears in the above-identified patent and that said Letters Patent are hereby corrected as shown below:

Column 16, line 30, change "$C_{20}H_{23}HO$" to --$C_{20}H_{23}NO$--;

Column 17, line 13, change "1.3-dihydro" to --1,3-dihydro--;

Column 19, line 39, change "[4-p-fluorophenyl)" to --[4-(p-fluorophenyl)--;

Column 19, line 44, change "benzoly)" to --benzoyl)--;

Column 22, line 11, change "1 to 6 atoms" to --1 to 6 carbon atoms--.

Signed and Sealed this

Seventh Day of September 1976

[SEAL]

Attest:

RUTH C. MASON
*Attesting Officer*

C. MARSHALL DANN
*Commissioner of Patents and Trademarks*